(12) United States Patent
Wilt et al.

(10) Patent No.: US 10,577,190 B2
(45) Date of Patent: Mar. 3, 2020

(54) DISC CONVEYOR FOR SAMPLE CUPS AND THE LIKE

(71) Applicant: The Innovative Technologies Group & Co., Ltd., Jessup, MD (US)

(72) Inventors: Robert R. Wilt, Chestertown, MD (US); Cornell S. Marschalko, Chesterfield, VA (US); Lou Faustini, Burtonsville, MD (US)

(73) Assignee: The Innovative Technologies Group & Co., Ltd, Jessup, MD (US)

( * ) Notice: Subject to any disclaimer, the term of this patent is extended or adjusted under 35 U.S.C. 154(b) by 20 days.

(21) Appl. No.: 15/766,242

(22) PCT Filed: Oct. 11, 2016

(86) PCT No.: PCT/US2016/056413
§ 371 (c)(1),
(2) Date: Apr. 5, 2018

(87) PCT Pub. No.: WO2017/062981
PCT Pub. Date: Apr. 13, 2017

(65) Prior Publication Data
US 2018/0282078 A1 Oct. 4, 2018

Related U.S. Application Data

(60) Provisional application No. 62/239,878, filed on Oct. 10, 2015.

(51) Int. Cl.
*B65G 47/28* (2006.01)
*G01N 21/13* (2006.01)
*B65G 43/08* (2006.01)

(52) U.S. Cl.
CPC ............. *B65G 47/28* (2013.01); *B65G 43/08* (2013.01); *G01N 21/13* (2013.01); *G01N 2021/135* (2013.01)

(58) Field of Classification Search
CPC ........ B65G 29/00; B65G 47/28; B65G 35/00; B65G 43/08; G01N 21/13
USPC ...................................... 198/459.3, 624, 786
See application file for complete search history.

(56) References Cited

U.S. PATENT DOCUMENTS

| 532,944 A | 1/1895 | Breed |
| 2,592,275 A | 4/1952 | Grosvenor |
| 2,597,930 A * | 5/1952 | Grosvenor .............. B21B 39/00 |
| | | 134/157 |
| 3,332,210 A * | 7/1967 | Tordi .................... B65B 7/2807 |
| | | 221/277 |

(Continued)

*Primary Examiner* — Douglas A Hess
(74) *Attorney, Agent, or Firm* — Royal W. Craig; Gordon Feinblatt LLC

(57) ABSTRACT

An improved disc feeder/conveyor (2) with optical sensor (200) and return chute (10) for multiple industrial, commercial or agricultural applications. The conveyor (2) comprises a pair of co-rotating (or counter-rotating) roller shafts (11A, 11B) driven by a belt (104) drive. The rollers (11A, 11B) are non-parallel, slightly angled, and the rotation of the shafts frictionally engages, the sample caps or other elements being advanced away from the production line causing the items seated thereon advance. Sensors (200, 202) detect the presence/absence of items on the rollers for gating. Another pair of co- or counter-rotating roller shafts (15A, 15B) may act as a return chute (10).

23 Claims, 5 Drawing Sheets

(56) References Cited

U.S. PATENT DOCUMENTS

| | | | |
|---|---|---|---|
| 3,827,582 A | 8/1974 | Lederer | |
| 3,886,892 A * | 6/1975 | Walls | B05B 13/0235 118/679 |
| 4,040,513 A * | 8/1977 | Walls | B05B 13/0235 198/530 |
| 4,226,207 A | 10/1980 | Genev et al. | |
| 4,312,172 A * | 1/1982 | Fisher | B65B 7/2807 221/14 |
| 4,391,560 A * | 7/1983 | Fardin | B65G 37/005 198/406 |
| 4,434,886 A | 3/1984 | Fajt | |
| 4,683,706 A * | 8/1987 | Harper | B65B 7/285 53/314 |
| 4,951,448 A * | 8/1990 | Schmechel | G07D 9/065 53/212 |
| 5,005,340 A * | 4/1991 | Mojden | B65B 5/067 377/6 |
| 5,087,423 A | 2/1992 | Ishibashi | |
| 5,135,103 A * | 8/1992 | Focke | B65B 41/12 198/786 |
| 5,355,991 A * | 10/1994 | Baranowski | A23L 3/001 198/412 |
| 5,806,686 A * | 9/1998 | Ecker | A23N 15/00 198/663 |
| 6,827,199 B1 * | 12/2004 | Amendolea | B23P 19/003 198/419.1 |
| 7,318,304 B2 * | 1/2008 | Hiddink | B65B 5/103 141/114 |
| 7,364,031 B1 * | 4/2008 | Johnson | B65G 47/252 198/419.2 |
| 7,828,134 B2 * | 11/2010 | Hatano | B65G 47/1492 198/397.04 |
| 8,622,196 B1 * | 1/2014 | Lapointe | B65G 33/06 198/383 |
| 9,751,741 B2 * | 9/2017 | Schraudolph | B67B 3/06 |
| 10,207,835 B2 * | 2/2019 | Wilhelm | B65B 7/2807 |

* cited by examiner

DISC CONVEYOR FOR SAMPLE CUPS AND THE LIKE

CROSS-REFERENCE TO RELATED APPLICATION(S)

The present application derives priority from U.S. application No. 62/239,878 filed 10 Oct. 2015.

BACKGROUND OF THE INVENTION

1. Field of the Invention

The present invention relates generally to feeder and conveyor mechanisms for disc-shaped objects and, more particularly, to a feeder/conveyor mechanism for optical sampling cups.

2. Description of the Background

Various applications require the linear transfer of small disc-shaped objects along process lines, batch operations or product storage locations for quality control, testing, packaging, labeling, surface treatment, painting/coating etc. This is true for a wide variety of disc-shaped objects such as neodymium magnets, rollers, pulley wheels, etc.

By way of example, agricultural and food production operations requires in line or periodic testing at predetermined intervals to ensure that food quality standards are being met. Many agricultural and food production operations rely on spectroscopic analysis to test materials with radiated energy, and there are many different variations of spectroscopic analyzers on the market today. Near-infrared (NIR) spectroscopy has greatly simplified and improved the speed of analysis for quality testing of grain, flours and beans. The use of near-infrared spectroscopy has led to higher sample throughput by replacing multiple time-consuming and complicated chemical techniques. Using NIR spectroscopy it is possible to non-destructively analyze inhomogeneous samples for moisture, protein, oil and many other parameters in less than one minute at all stages of production: grading, milling, oil extraction and final product quality verification. In most large scale operations such as grain processing, representative samples of the product are tested at predetermined internals. Commercial grain analyzers suitable for this purpose in grain production operations are currently available under the trade names FOSS® and NIRSYSTEMS®, among others. These and many other analyzers use "sample cups." An amount of grain is deposited into a disc-shaped sample cup which has one or more windows, and measurements of radiation transmitted through or reflected through the grain via the window(s) is analyzed. Traditional grain analysis systems require an operator to monitor the process line and to manually remove representative samples of grain from the process line for testing by, i.e., transporting the samples by hand from the process line and depositing them into the sample cups, then hand-feeding into a grain analyzer individually. Such systems suffer from the additional manpower needed to monitor and select representative samples, transport them to the grain analyzer and monitor the progress of grain analysis before manually returning the sample container and/or the sample to the product line to repeat the process. Attempts have been made to automate the process. For example, U.S. Pat. No. 5,087,423 to Ishibashi issued Feb. 11, 1992 shows a modular analyzer in which sample cups are automatically transported and distributed via conveyer belts. Unfortunately, when it comes to feeding disc-shaped objects into a precise position at finely-timed intervals, conveyer belts do not provide the measure of control necessary.

It is also known that disc-shaped objects can be cradled on a pair of spaced cylindrical support rollers mounted side-by-side, and can be linearly conveyed there along. For example, U.S. Pat. Nos. 3,886,592 and 4,040,513 both to Walls describe a device for applying paint to one or more similarly sized and shaped discs as they are advanced along a production line. Walls' device includes a pair of generally cylindrical support rollers rotatably mounted in adjacent side-by-side relationship to provide a cradle for supporting a row of similar discs or the like on edge in adjacent relationship. The support rollers extend in parallel downward at an incline from the bearing supports, and are rotated in the same angular direction so that adjacent surfaces of the rollers move in opposite directions to both spin and advance the discs along the rollers from one end to the other. Advancement is acid to work by a gyro phenomenon called precession, with the discs spinning and tipped forward the tendency of the discs to fall forward urges them longitudinally down the support rollers.

In addition, U.S. Pat. No. 4,226,207 to Genev et al. describes an apparatus for applying protective coatings to cylindrical graphite bodies, in which a pair of shafts are axially offset. A disk rides in full contact against one shaft and in point contact with the other, switching at the crossover point of the shafts, the rotational force of the point contact advancing the disk along the shafts. To wit, the prior art feeding mechanisms disclosed by Genev and Walls are designed for in-line processes where no return chute is needed.

In addition, the accuracy of the conventional process of analyzing samples from a production line comprising grain or other agricultural or non-agricultural goods also suffers with greater variability in intervals between samples as they are taken from the production line. Ideally, for the best sample accuracy, a sample is removed from the process line and transferred immediately to a grain analyzer or other sampling device without delay, so that testing occurs as soon as possible after the sample is removed from the line. With grain, as with other types of agricultural goods and other selected products, defects occur in a non-random fashion due to differences in the way that batches of crops are grown, harvested, stored, etc. When samples from the production line are tested as soon as possible after being removed from the line, any samples that do not meet quality control standards may be noted as soon as possible and the batch(es) corresponding to same may be removed from production or otherwise corrected earlier in the process.

Accordingly, what is needed is a feeder/conveyor for sample cups that allows a human operator to fill a plurality of sample cups with materials to be analyzed, load those sample cups into a queue on the feeder/conveyor, the feeder/conveyor thereupon automating the infeed of the queued sample cups into an analyzer on an as-needed basis so that samples are tested as soon as possible after being removed from the fine. Also what is needed is a feeder/conveyor for sample cups that allows a human operator to load tested sample cups ejected from the analyzer back onto a return queue on the feeder/conveyor for prompt disposition.

SUMMARY OF THE INVENTION

Accordingly, it is an object or the present invention to provide an improved feeder/conveyor for disc-shaped objects such as sample cups that employs rotating spaced cylinders disposed at a small acute angle for efficiently and automatically forming an inked queue and transporting multiple disc elements such as sampling cups at the infeed of a grain analyzer for on-demand-processing.

It is another object of the invention to provide an improved feeder/conveyor that automatically queues and transports multiple disc elements along a return line after testing at the grain analyzer.

It is another object of the invention to provide an improved feeder/conveyor as described above in which the inked queue and return queue are driven by a single drive mechanism.

It is also an object of the present invention to provide such an improved disc feeder/conveyor comprising sensors at the inked queue and return queue for detecting the presence of elements on the rollers.

These and other features and benefits are achieved with an improved disc conveyor for sample cups and the like with both an inked queue and return queue, both queues utilizing a pair of rotating spaced roller shafts driven by a belt drive. The rollers are non-parallel, slightly angled, and the rotation of the shafts frictionally engages the sample cups or other elements being advanced away from the production line causing the items seated thereon advance. Optional sensors detect the presence/absence of items in the infeed queue and return queue for automatic gating. In addition, a single belt drive mechanism drives both infeed queue and return queue rollers efficiently and quietly for long term use.

For a more complete understanding of the invention, its objects and advantages refer to the remaining specification and to the accompanying drawing.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENTS

Figure 1:
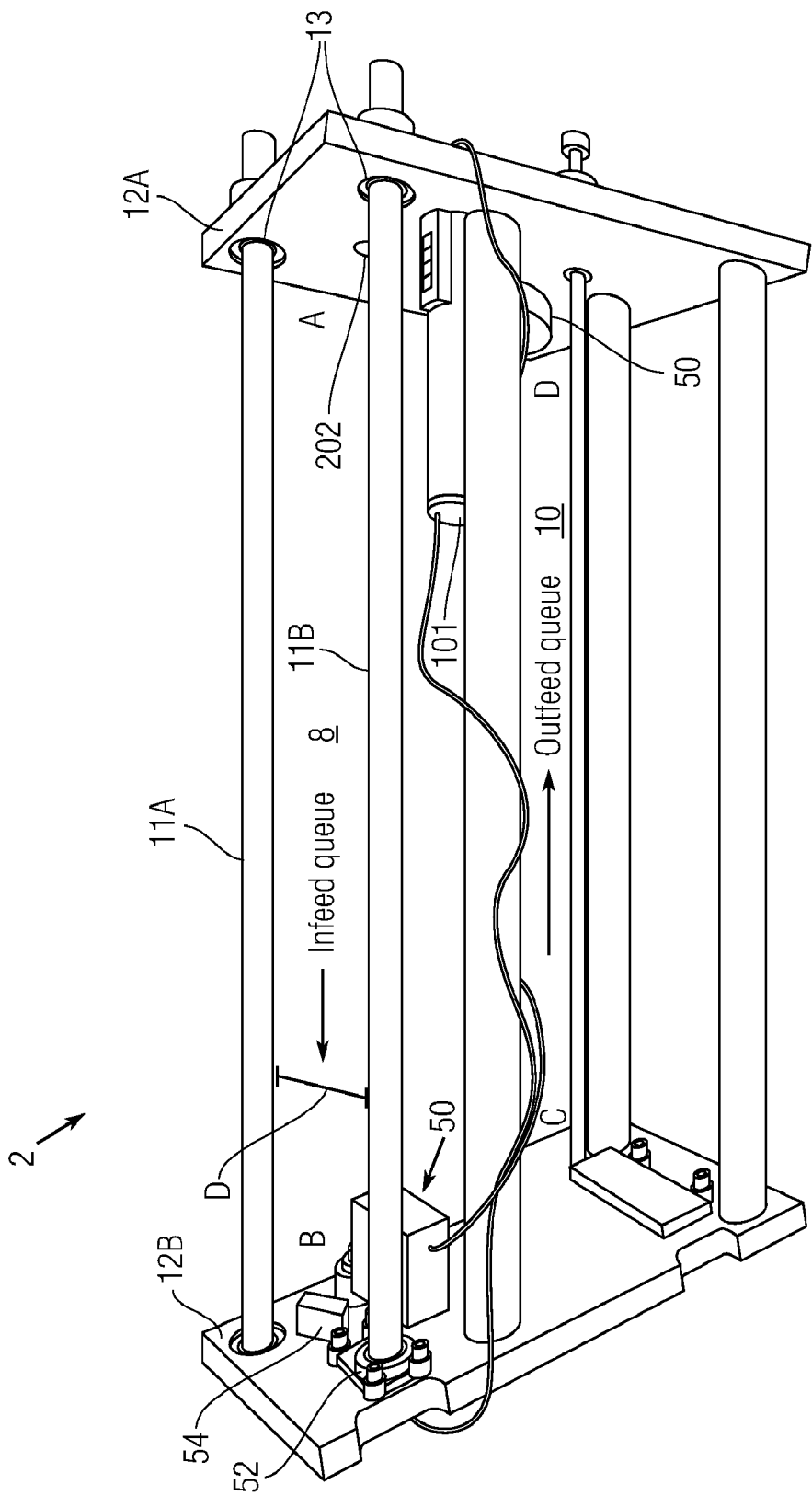
FIG. 1 is a front perspective view of the improved disc feeder/conveyor with optical sensors according to the present invention.

With reference to FIG. 1, the disc feeder/conveyor 2 according to the present invention comprises an infeed queue 8 for stacking, transporting, and queueing multiple disc elements in one direction, and one-by-one ejecting them on-demand into the infeed of a grain analyzer or any other equipment, and an outfeed queue 10 for stacking, transporting, and queueing the same disc elements after processing by and ejection from the grain analyzer. The transport direction of the indeed queue 8 runs linearly along two elongate cylindrical roller bars 11A, 11B that extend between oppos- ing roller mounts 12A, 12B. The transport direction of the outfeed queue 10 runs opposite the infeed queue 8, linearly along two elongate cylindrical roller bars 11C, 11D that extend between opposing roller mounts 12A, 12B. Roller mounts 12A, 12B may take any form suitable for supporting roller bars 11A-D in a roughly horizontal position and for providing means by which to couple roller bars 11A-11D to drive mechanism 100 (see FIG. 6) as will be described herein. Toward this end roller mounts 12A, 12B may take the form of solid, vertically-extended brackets hazing a small width in a direction roughly parallel to that of roller bars 11A-11D, such that the ends of roller bars 11A-11D may pass there through to access drive mechanism 100. In a preferred embodiment roller mounts 12A, 12B are L- or Z-shaped brackets, spaced apart such that the infeed roller bars 11A, 11B and outfeed roller bars 11C, 11D are supported there between. Roller mounts 12A, 12B are dimensioned such that the ends of the infeed roller bars 11A, 11B may be supported side-by-side in a spaced relation, and the ends of the outfeed roller bars 11C, 11D are likewise supported side-by-side below the two juiced roller bars 11A, 11B with sufficient clearance to accommodate travel of the sample cups there along, and to allow open access for depositing disc elements onto the two infeed roller bars 11A, 11B and for removing disc elements from the two outfeed roller bars 11C, 11D. One skilled in the art will readily understand that roller mounts 12A, 12B may be any sort of supporting members capable of supporting roller bars 11A-D, such as the sides of a partially enclosed housing or casing, an assembled frame of struts, an existing analyzer machine, or the like.

In operation, grain analyzer sample cups are loaded into and queued by the disc feeder/conveyor 2 for on-demand loading into the infeed of an analyzer or other device. The infeed may any single-disc slot, or multiple-disc infeed such as a carousel or turret-system as shown in U.S. Pat. No. 6,117,391 to Mootz et al. Loading onto the disc feeder/conveyor 2 may be manual or automated. For example, an operator may manually load sample cups onto the infeed roller bars 11A, 11B at point A (FIG. 1) of the analyzer and the sample cups are automatically transported down to point B where they are queued, and on-demand ejected by a first servo-controlled gate 50 attached to roller mount 12B. One skilled in the art will understand that sample cups may by automatically loaded onto the disc feeder/conveyor 2 by some external hopper assembly (not shown).

As shown in FIG. 1 first servo-controlled gate 50 includes a fixed gate post 52 for admitting a single disc element into the gate 50, and a kicker arm 54 for ejecting a single disc element off the infeed roller bars 11A, 11B at point B (FIG. 1) through the gate post 52 into the infeed of an adjacent analyzer (not shown). Operation is similar for the outfeed queue, where loading may be manual or automated. For example, an operator may manually load already-analyzed sample cups ejected from the analyzer onto the outfeed roller bars 11C, 11D at point C (FIG. 1) and the sample cups are automatically transported down to point D where they are queued, and manually removed or, if desired, removed automatically and on-demand by a robot arm or the like, or ejected by a second servo-controlled gate 50 attached to roller mount 12A. The second servo-controlled gate 50 likewise includes a fixed gate post 52 for passing only a single disc element, and a kicker arm 54 for ejecting a single disc element off the outfeed roller bars 11C, 11D at point D (FIG. 1) through the gate post 52 into a hopper tray or other receptacle (not shown).

Figure 4:
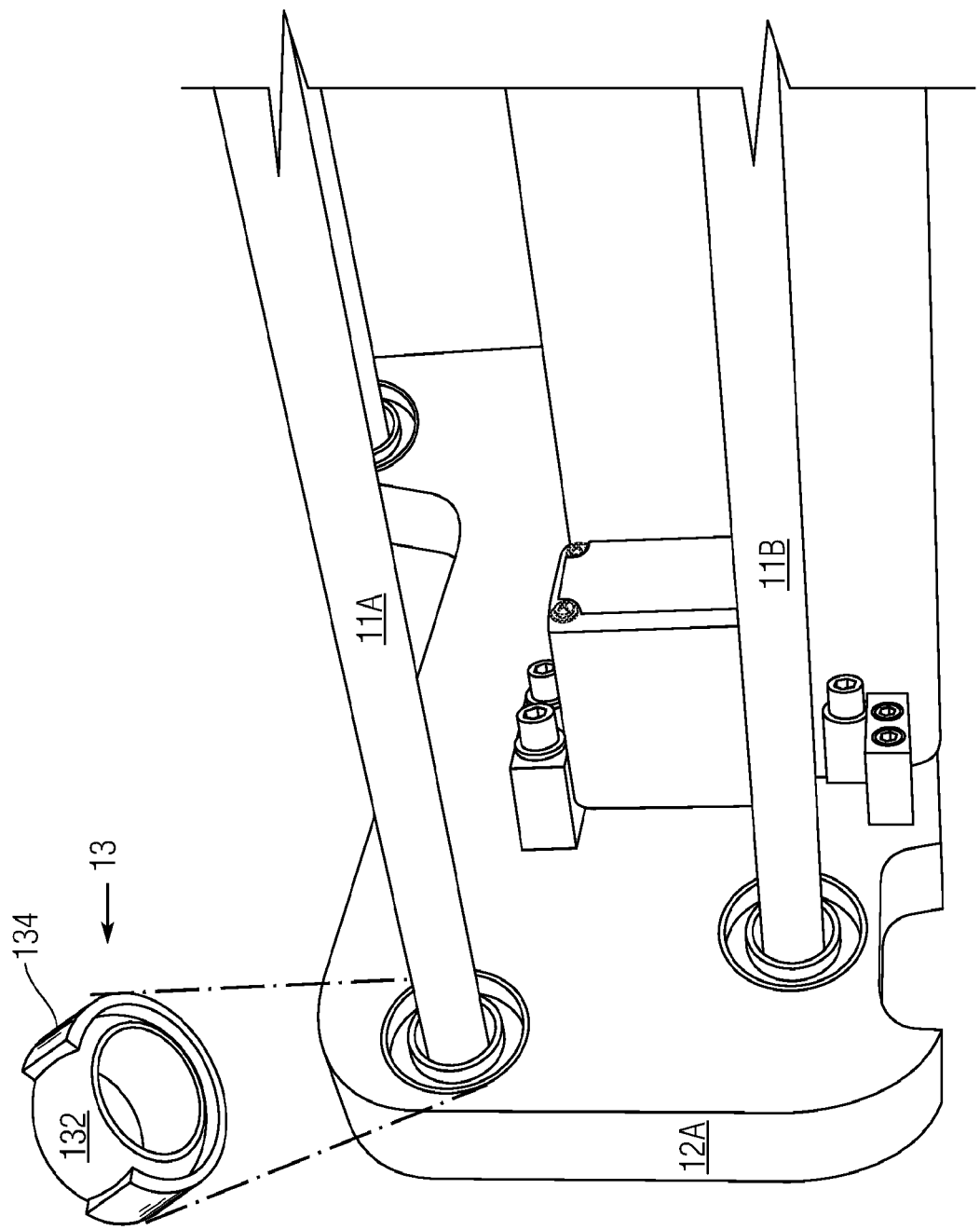
FIG. 4 is a top partial-perspective view of the improved disc feeder/conveyor according to the present invention showing a close up of optical sensor 200.

Preferably, roller mounts 12A, 12B each have a solid planer face defined by oversized through-holes for each roller 11A-D, said through-holes being equipped with bearings 13 such that roller bars 11A-D are rotatably journaled within or through through-holes and able to be rotated by drive mechanism 100 with minimal friction from roller mounts 12A, 12B. In a preferred embodiment the bearings 13 are spherical-bearings that permit angular rotation about a central point in two orthogonal directions. Each spherical bearing 13 includes a hemispherical inner ring 112 (see FIG. 4) inserted onto the end of each roller bar 11A-D, the inner ring 132 being held captive within an outer ring 134 in the axial direction only. However, the inner ring 132 remains free to revolve by a limited degree within the outer ring 134 to accommodate a limited range of axial alignments. These spherical bearings 13 are each journaled into their respective through-holes. These spherical double bearing assemblies 13 ensure quiet frictionless rotation.

Roller bars 11A-D may be formed of any material known in the art that is rigid and sturdy enough to support the weight of several disc elements such as grain analyzer sampling cups filled with grain or any other disc shaped objects for a bulk feed operation or the like. Thus, roller bars 11A-D are preferably stainless steel, but may be any other metal, metal alloy, composite, or plastic of sufficient strength and durability to withstand repeated rotation by drive mechanism 100 through bearings 13 at relatively high rates of angular rotation when loaded with sampling cups or other objects for an extended period of time.

Figure 2:
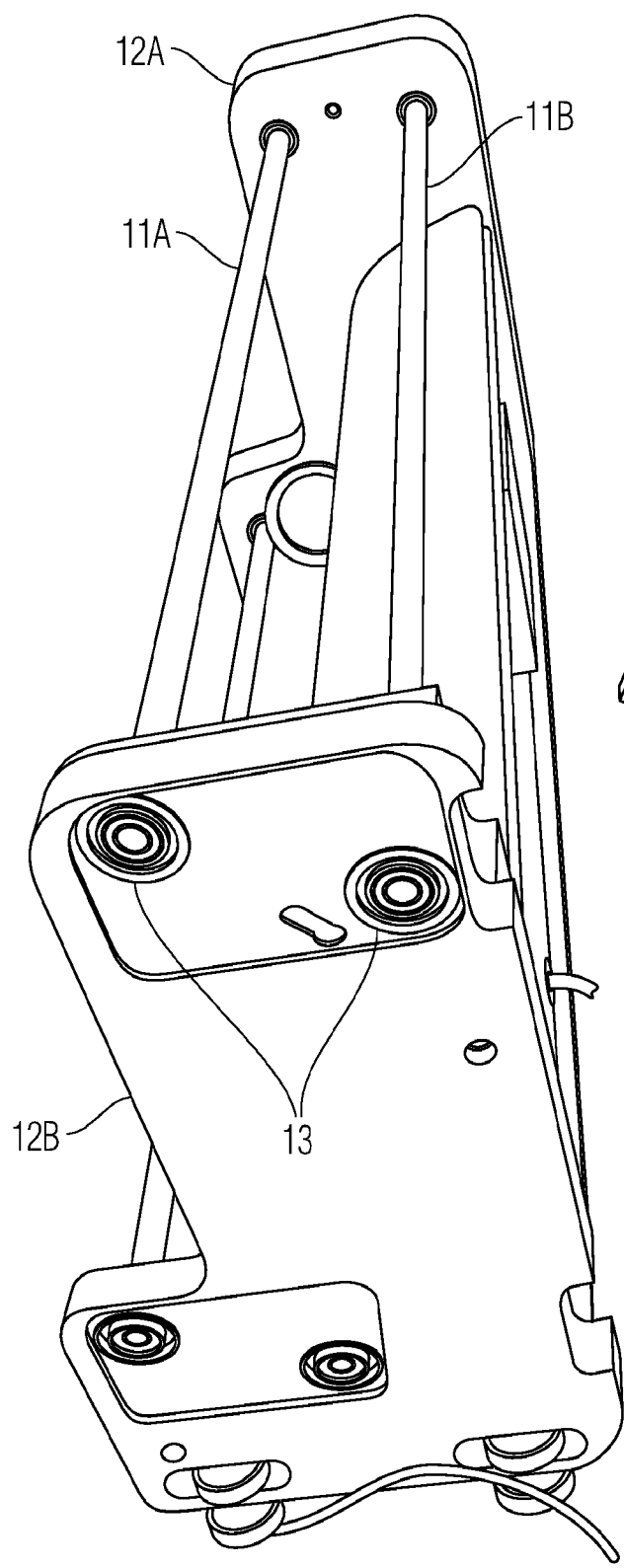
FIG. 2 is a side perspective illustration of the improved disc feeder/conveyor according to the present invention.
Figure 3:
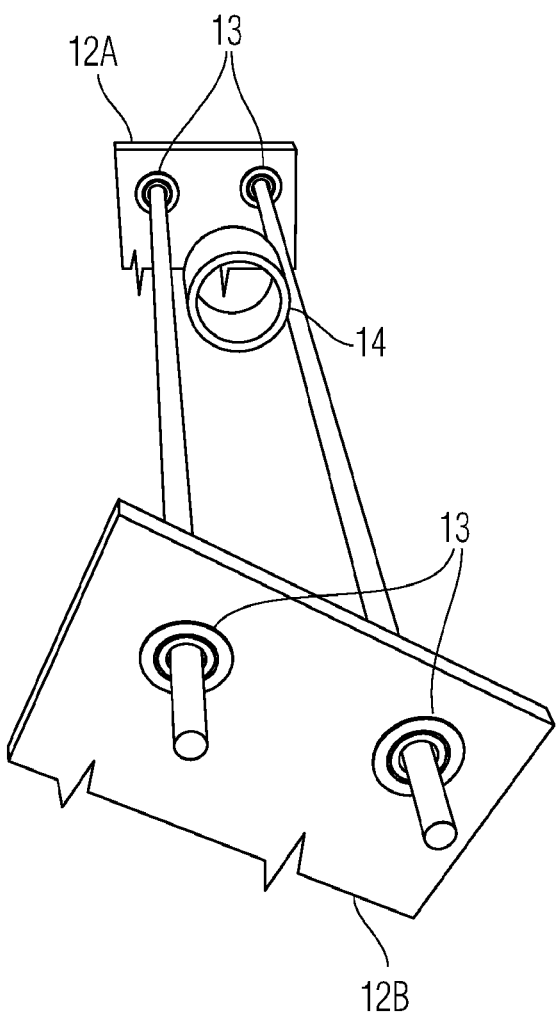
FIG. 3 is a side perspective illustration of the improved disc feeder/conveyor according to an alternate embodiment of the present invention depicting non-parallel roller mounts 12A, 12B.

As best seen in FIG. 1, infeed roller bars 11A, 11B are preferably aligned close to a horizontal plane formed at a right angle to both roller mounts 12A, 12B. Infeed roller bars 11A, 11B are uniformly spaced along their entire lengths by equal spacing of each pair of bearings 13 in roller mounts 12A, 12B. However, the pair of bearings 13 in roller mount 12A is angularly offset (twisted) relative to the pair of bearings in roller mount 12B, resulting in non-parallel yet uniformly-spaced roller bars 11A, 11B. This angular twist causes the roller bars 11A, 11B to form a slight acute angle (nominally 3.5 degrees and preferably within a range of from 0.5 to 5 degrees) relative to each other, with the end of roller bar 11B dropping below that of roller bar 11A at roller mount 12B so that the kicker arm 54 of the first servo-controlled gate 50 can easily eject disc elements off the roller bars 11A, 11B. One skilled in the art will understand that the rotation speed of roller bars 11A, 11B and the degree of twist/angle of roller bars 11A, 11B determines the speed of advancement of sample cups, and said speed may be increased or decreased as desired by increasing/decreasing, the rotation speed of roller ban 11A, 11B and/or the degree of twist/angle. Thus, as shown in FIG. 2, through-holes comprising bearings 13 in roller mount 12A are angularly offset relative to bearings 13 in roller mount 12B but are equally-spaced such that a sample cup carried thereon follows a straight horizontal path. Alternatively, as a matter at design choice as shown in FIG. 3, both roller mounts 12A, 12B may be advisably affixed to other equipment within a process line such that the overall twist of roller bars 11A 11B, or angle formed by roller bars 11A, 11B relative to one another, is adjustable. Either one of roller bars 11A, 11B may be disposed perpendicularly to both roller mounts 12A, 12B so long as the other roller bar forms an angle relative thereto. In the preferred embodiment, as illustrated in FIGS. 1-3, both roller bars 11A, 11B are equally angularly-offset such that roller bar 11B inclines downward toward its lowest point at roller mount 12B so that as disk element 14 (sampling cup) (shown in FIG. 3) advancing towards roller mount 12B can be ejected more easily from roller mechanism 10 towards the side proximate the downward sloped roller 11B in a consistent and repeatable fashion.

Roller bars 11A, 11B are preferably separated by a distance D at both roller mounts 12A and 12B, wherein D is slightly less than the diameter of the disc element 14 being conveyed by the device 10. It will be understood that, although the spacing may change along the length of roller bars 11A, 11B, a uniform spacing provides a uniform rate of advancement. As an alternative to servo-controlled gates 50, the system 10 may be designed to deposit discs 14 by angling the roller bars 11A, 11B so that the center of gravity of discs 14 crosses the axis of roller bar 11B at the outfeed position such the discs 14 simply fall off. Alternatively, the spacing between roller bars 11A, 11B may be progressively widened to a spacing D+n at the outfeed that is slightly greater the diameter of the disc element 14, so that the disc elements 14 falls through the roller bars 11A, 11B to the bottom of the device, as opposed to ejection over the side of same. Of course, the point of drop must coincide with the input of the grain analyzer, conveyor, or other desired location underneath roller bars 11A, 11B where the discs 14 are to be deposited.

The outfeed roller bars 11C, 11D are configured exactly as described above though the twist angles and inclines are preferably reversed. As described, roller bars 11C, 11D are for returning a disc element 14 to a starting or secondary offload position, either to a point along the process line, at a secondary inspection station, at a waste station, or the like. Like infeed roller bars 11A, 11B, outfeed roller bars 11C, 11D are preferably mounted on roller mounts 12A, 12B within through holes comprising bearings 13 and at or close to the horizontal plane formed at a right angle to both roller mounts 12A, 12B but forming a slight twist angle relative to each other. Return roller bars 11C, 11D are shown in, i.e., FIGS. 2 and 5 as being disposed below roller bars 11A, 11B, but alternative configurations are possible as necessary to deliver disc elements 14 to the desired locations.

Figure 5:
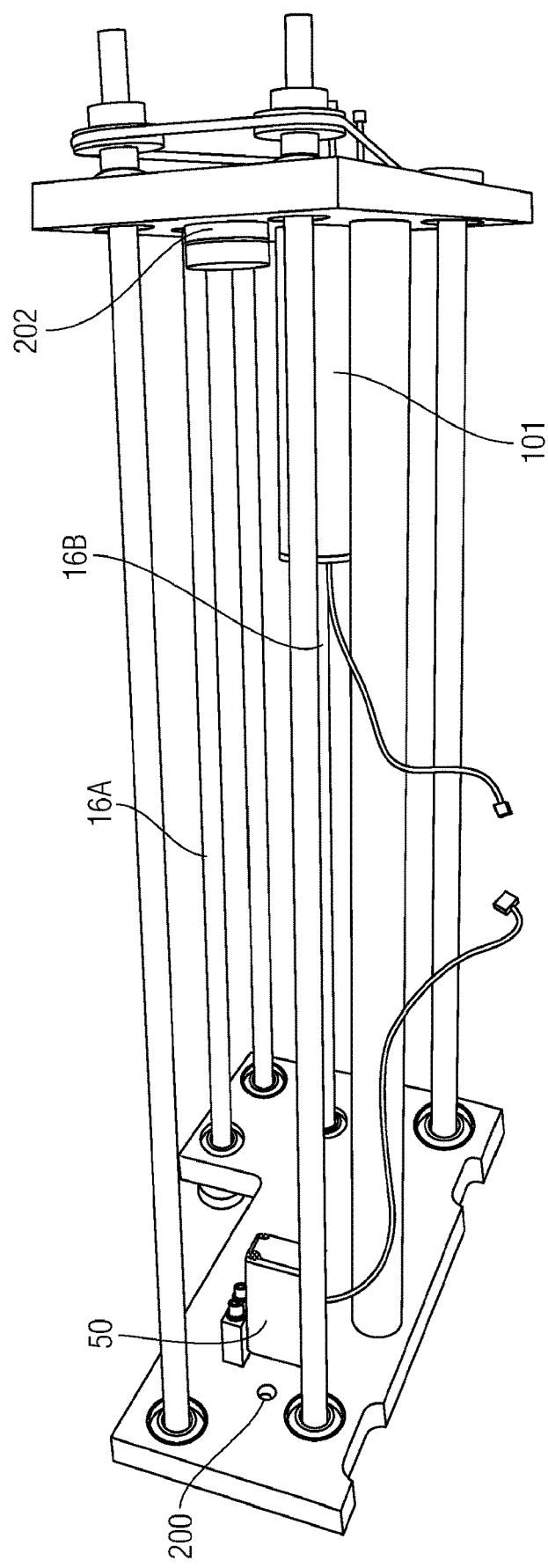
FIG. 5 is a top perspective illustration of the improved disc feeder/conveyor according to the present invention.
Figure 6:
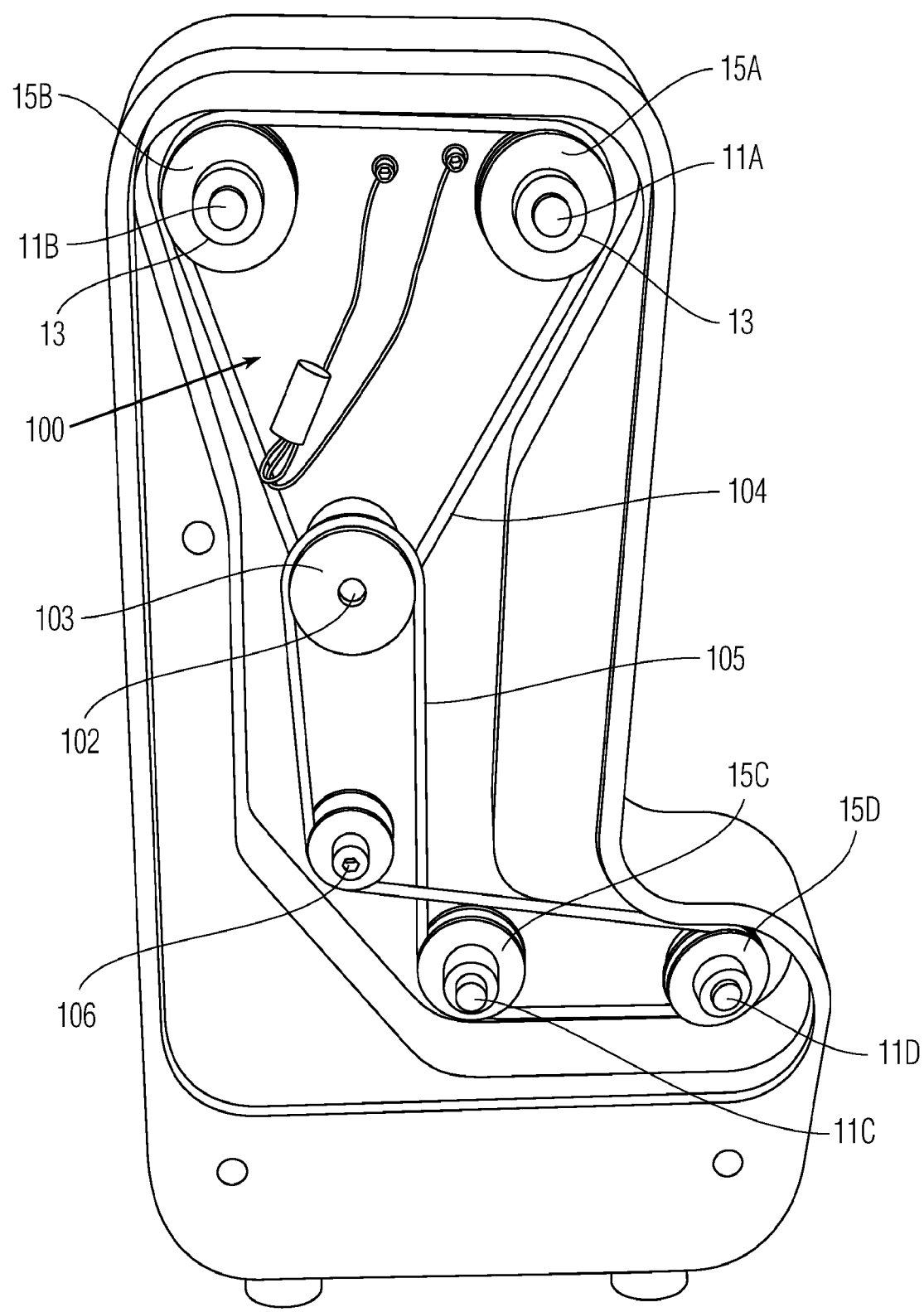
FIG. 6 is a side perspective illustration of the improved disc feeder/conveyor according to the present invention depicting drive mechanism 100.

FIG. 6 depicts the drive mechanism 100 for roller bars 11A, 11B. As shown therein, roller bars 11A-11D protrude through through-holes comprising bearings 13 in roller mount 12A where they are fitted with circumferential pulleys 15A-15D for interfacing with drive mechanism 100. In the preferred embodiment drive mechanism 100 comprises a motor 101 (see FIG. 5), which may be mounted in various locations relative to roller bars 11A, 11B but which is shown herein as being mounted underneath roller bars 11A, 11B and above roller bars 11C, 11D on the inside face of roller mount 12A. Referring back to FIG. 6, the motor 101 extends a drive shaft 102 through roller mount 12A on which is affixed a double-wheel pulley 103. A first belt 104 is run around pulleys 15A, 15B and one side of double-wheel pulley 103. A second belt 105 is run around pulleys 15C, 15D and the other side of double-wheel pulley 103, and this second belt is folded over around an offset free-wheeling pulley 106 to effect rotation. This way, roller bars 11A, 11B rotate in the same angular direction to advance disc element(s) 14. In this arrangement, first belt 104 is driven by drive shaft 102 via double pulley 103 and drives the pulleys 15A, 15B of roller bars 11A, 11B in a circular co-rotating fashion (clockwise in FIG. 6), the angular direction and momentum of drive shaft 102 dictating the angular direction and momentum of roller bars 11A, 11B. The second belt 105 may be connected to drive shaft 102 and to outfeed roller bars 15C, 15D via free-wheel pulley 106 to effect synchronous co-rotation of roller bars 15C, 15D in the same manner, thereby accomplishing an identical infeed and outfeed transfer rate with a single motor.

In other embodiments, each pair of infeed roller bars 11A, 11B and/or outfeed roller bars 15C, 15D may be counter rotating. To effect counter-rotation of infeed roller bars 11A, 11B, drive shaft 102 may be connected to an additional free-wheel pulley 106 (not shown) located between roller bars 11A, 11B and the belt 104 folded over thereabout, such that belt 104 provides an opposite angular momentum to roller bars 11A and 11B. Similarly, the location and orientations of belt 105 may be reconfigured to provide counter-rotation to return rollers 15C, 15D in the same manner. Belts 104, 105 may be made of a flexible rubber material such that they can be removed and replaced or reconfigured to change the relative angular momentums of roller bars 11A-11D.

As seen in FIG. 5, another advantageous feature of the present invention is a reflectance sensor 200 mounted in an aperture in roller mount 12B located between roller bars 11A, 11B and directed along the roller bars 11A, 11B. Reflectance sensor 200 comprises a single infrared LED and phototransistor pair in a compact module that can be panel-mounted in either roller bracket 12A, 12B to project an infrared light beam toward disc elements 14. When disc elements 14 are present they reflect the light back to the reflectance sensor 200 signaling their presence, and when the queue is empty no light is reflected and absence of any disc element is signaled. This allows selective gating/ejection of disc elements 14 and thereby improves efficiency of the process of removing and/or returning discs 14 within a production facility. A similar reflectance sensor 202 may be mounted in an aperture in roller mount 12A located between roller bars 11C, 11D for accomplishing the same along the outfeed path. The reflectance sensors 200, 202 may be operatively connected to the analyzer processor to avoid a backlog of discs 14 on roller bars 11A-11D while one sample is being analyzed, or to account for any variability in processing time. Reflectance sensors 200, 202 may also be coupled to a conveyor belt or other mechanism that feeds discs 14 onto roller bars 11A, 11B, or may provide a visual or audio alert indicating the readiness of device 10 for manual loading of another disc 14, and/or for manual off-loading to further avoid a backlog of discs while a previous disc is processing.

Although described herein with reference to a process of feeding sample cups 14 into a grain analyzer, it should be understood that the inventive device 10 may be used in any industrial, agricultural, or commercial process requiring the advancement of disc-like objects from one area to another with minimal electrical output and with the ability to gate said objects for optimal spacing thereof.

Having now fully set forth the preferred embodiments and certain modifications of the concept underlying the present invention, various other embodiments as well as certain variations and modifications of the embodiments herein shown and described will obviously occur to those skilled in the an upon becoming familiar with said underlying concept. It is to be understood, therefore, that the invention may be practiced otherwise than as specifically set forth in the appended claims.

STATEMENT OF INDUSTRIAL APPLICABILITY

There are numerous industrial applications that require the linear transfer of small disc-shaped objects along process lines, batch operations or product storage locations for quality control, testing, packaging, labeling, surface treatment, painting/coating, etc. This is particularly true for commercial grain analyzers which use disc-shaped sample cups that are hand-loaded into the grain analyzer individually. Despite attempts at automating the process, it has proved difficult to feed disc-shaped objects into a precise position at finely-timed intervals. There would be great industrial applicability in a disc feeder/conveyor that can be readily interfaced to a conventional grain analyzer or other device to queue sample cups and transfer them on-demand immediately into a grain analyzer without delay, so that testing occurs as soon as possible after the sample is loaded into the sample cup. The foregoing would allow a human operator to fill a plurality of sample cups with materials to be analyzed, load those sample cups into a queue on the feeder/conveyor, the feeder/conveyor thereupon automating the infeed of the queued sample cups into an analyzer on an as-needed basis so that samples are tested as soon as possible after being removed from the line. Also, sample cups can be ejected from the analyzer back onto a return queue on the feeder/conveyor for prompt disposition.

We claim:

1. A feeder/conveyor apparatus for queuing a plurality of uniform disc-shaped objects into and from an adjacent piece of equipment, the apparatus comprising:
   a supporting frame including a pair of upstanding supports spaced apart and oriented in parallel places;
   a first pair of linear but non-parallel rods, said rods being rotatably journaled in said pair of upstanding supports and traversing said supports at an intermediate distance less than a diameter of said disc-shaped objects;
   a second pair of linear rods rotatably journaled in said pair of upstanding supports and traversing said supports at said intermediate distance;
   a drive mechanism mounted on said frame for co-rotating said first pair of non-parallel rods and said second pair of non-parallel rods; and
   a first sensor mounted on one of said upstanding supports proximate said first pair of non-parallel rods for detecting said disc-shaped objects on said first pair of non-parallel rods.

2. The feeder/conveyor apparatus according to claim 1, wherein said first pair of non-parallel rods are angularly twisted non-parallel.

3. The feeder/conveyor apparatus according to claim 2, wherein said first pair of non-parallel rods are angularly twisted within a range of from 0.5 to 5 degrees.

4. The feeder/conveyor apparatus according to claim 1, wherein said second pair of non-parallel rods are non-parallel.

5. The feeder/conveyor apparatus according to claim 4, wherein said second pair of non-parallel rods are angularly twisted.

6. The feeder/conveyor apparatus according to claim 4, wherein said second pair of non-parallel rods is rotatably journaled said pair of upstanding supports below said first pair of non-parallel rods.

7. The feeder/conveyor apparatus according to claim 4, further comprising a second sensor mounted on one of said upstanding supports proximate said second pair of non-parallel rods for detecting said disc-shaped objects on said second pair of non-parallel rods.

8. The feeder/conveyor apparatus according to claim 7, wherein said first sensor and second sensor comprise reflectance sensors.

9. The feeder/conveyor apparatus according to claim 4, wherein each end of said second pair of parallel rods is rotatably journaled into said pair of upstanding supports via a spherical bearing.

10. The feeder/conveyor apparatus according to claim 4, wherein said drive mechanism comprises a motor, a plurality of pulleys mounted on each of said first pair of non-parallel rods, said second pair of non-parallel rods, and said motor, and a drive belt wound about said plurality of pulleys.

11. The feeder/conveyor apparatus according to claim 1, wherein each end of said first pair of parallel rods is rotatably journaled into said pair of upstanding supports via a spherical bearing.

12. The feeder conveyor apparatus according to claim 1, further comprising a first gate mechanism for ejecting a single disc-shaped object from said first pair of parallel rods.

13. The feeder/conveyor apparatus according to claim 12, further comprising a second gate mechanism for ejecting a single disc-shaped object from said second pair of parallel rods.

14. A feeder/conveyor apparatus for queuing a plurality of uniform disc-shaped objects into and from an adjacent piece of equipment, the apparatus comprising:
a supporting frame including a pair of upstanding supports spaced apart and oriented in parallel places;
a first pair of linear but non-parallel rods, said rods being rotatably journaled in said pair of upstanding supports and traversing said supports at an intermediate distance less than a diameter of said disc-shaped objects;
a drive mechanism mounted on said frame for co-rotating said first pair of non-parallel rods said drive mechanism further comprising a motor, a plurality of pulleys mounted on each of said first pair of non-parallel rods and said motor, and a drive belt wound about said plurality of pulleys; and
a first sensor mounted on one of said upstanding supports proximate said first pair of non-parallel rods for detecting said disc-shaped objects on said first pair of non-parallel rods.

15. A feeder/conveyor apparatus for queuing a plurality of sample cups into and out from a spectrometer, comprising:
a supporting frame;
an infeed queue comprising a first pair of linear non-parallel rods rotatably journaled in said frame;
an outfeed queue comprising a second pair of linear non-parallel rods rotatably journaled in said frame;
a drive mechanism mounted in said frame for co-rotating said first pair of non-parallel rods, and for co-rotating said second pair of non-parallel rods.

16. The feeder/conveyor apparatus according to claim 15, further comprising an infeed sensor for detecting said disc-shaped objects on said first pair of non-parallel rods.

17. The feeder/conveyor apparatus according to claim 16, further comprising an outfeed sensor for detecting said disc-shaped objects on said second pair of non-parallel rods.

18. The feeder/conveyor apparatus according to claim 15, wherein said first pair of non-parallel rods are angularly twisted non-parallel, and said second pair of non-parallel rods are angularly twisted non-parallel.

19. The feeder/conveyor apparatus according to claim 18, wherein both of said first and second pair of non-parallel rods are angularly twisted within a range of from 0.5 to 5 degrees.

20. The feeder/conveyor apparatus according to claim 15, further comprising a first gate mechanism for ejecting a single disc-shaped object from said infeed queue.

21. The feeder/conveyor apparatus according to claim 20, further comprising a second gate mechanism for ejecting a single disc-shaped object from said outfeed queue.

22. The feeder/conveyor apparatus according to claim 15, wherein each end of said first and second pairs of parallel rods are rotatably journaled into said flame via a spherical bearing.

23. The feeder/conveyor apparatus according to claim 15, wherein said drive mechanism comprises a motor, a plurality of pulleys mounted on each of said first and second pairs of non-parallel rods and said motor, and a drive belt wound about said plurality of pulleys.

* * * * *